(12) United States Patent
Burgess et al.

(10) Patent No.: US 8,057,509 B2
(45) Date of Patent: Nov. 15, 2011

(54) MULTI-TOOL TWEEZER

(75) Inventors: Patrick Burgess, Jalisco (MX); Tyler Garland, Studio City, CA (US); Aldias Rauda, West Hollywood, CA (US); Stan Chudzik, Alpharetta, GA (US); Christian Hartsfield, Atlanta, GA (US)

(73) Assignee: Goody Products, Inc., Atlanta, GA (US)

( * ) Notice: Subject to any disclaimer, the term of this patent is extended or adjusted under 35 U.S.C. 154(b) by 469 days.

(21) Appl. No.: 12/122,830

(22) Filed: May 19, 2008

(65) Prior Publication Data
US 2008/0300623 A1    Dec. 4, 2008

Related U.S. Application Data

(63) Continuation-in-part of application No. 11/928,439, filed on Oct. 30, 2007, now abandoned, which is a continuation-in-part of application No. 29/275,604, filed on Dec. 30, 2006, now Pat. No. Des. 559,459.

(51) Int. Cl.
*A61B 17/50* (2006.01)
(52) U.S. Cl. .................................................. 606/210
(58) Field of Classification Search .............. 606/131, 606/133, 210, 211; 294/3, 99.1, 99.2; D24/143; D28/55
See application file for complete search history.

(56) References Cited

U.S. PATENT DOCUMENTS

| | | | |
|---|---|---|---|
| 1,889,475 A | 1/1932 | Henkel | |
| 2,406,393 A | 9/1943 | Neugass | |
| 2,334,252 A * | 11/1943 | MacGregor | 294/99.2 |
| 2,634,728 A * | 4/1953 | Dale | 606/210 |
| 3,287,547 A | 6/1964 | Spedding | |
| 3,510,204 A | 4/1967 | Jack | |
| 4,401,434 A | 8/1983 | Harris | |
| 4,474,543 A | 10/1984 | Hart | |
| 4,836,596 A | 6/1989 | Owen | |
| 5,190,335 A | 3/1993 | Rommerdale | |
| 5,334,215 A | 8/1994 | Chen | |
| 5,358,297 A | 10/1994 | Coleman | |
| 5,740,611 A | 4/1998 | Schloss | |
| 5,899,513 A | 5/1999 | Grisoni | |
| 6,179,847 B1 | 1/2001 | Possum | |
| D456,076 S | 4/2002 | Tyler | |
| 6,502,587 B1 | 1/2003 | Kellum | |
| 6,866,314 B2 | 3/2005 | Cho | |
| D521,685 S | 5/2006 | Cho | |
| 7,083,210 B2 | 8/2006 | Muramatsu | |
| 7,178,847 B1 | 2/2007 | Mui | |
| 7,229,111 B2 | 6/2007 | Cohen | |

* cited by examiner

*Primary Examiner* — Ryan Severson
(74) *Attorney, Agent, or Firm* — Lempia Summerfield Katz LLC

(57) ABSTRACT

The present disclosure is generally directed to a multi-tool with more than one tweezer tip. In an example embodiment the multi-tool includes two plates and an interposed spring component. The plates have a plurality of tweezer tip pairs and the spring component permits pivoting articulation of the plates in order to apply pinching forces by the different tweezer tip pairs upon an area of interest.

12 Claims, 11 Drawing Sheets

MULTI-TOOL TWEEZER

RELATED APPLICATION

This continuation-in-part application claims the priority benefit of U.S. patent application Ser. No. 11/928,439, filed on Oct. 30, 2007 now abandoned, which is a continuation-in-part of U.S. Design patent application Ser. No. 29/275,604, filed on Dec. 30, 2006 now U.S. Pat. No. D559,459, the contents of both of which are incorporated by reference as if fully expressed fully herein.

FIELD OF THE DISCLOSURE

The present disclosure is generally directed to a multi-tool with more than one tweezer.

BACKGROUND OF THE DISCLOSURE

Most types of tweezers are generally of a uniform size and are designed for use by women. These types of tweezers may not be suitable for use by men. Current tweezers are designed mainly with women's ergonomic/human-factor measurements in mind, meaning that they are designed for smaller hands and fingers. The small size of tweezers may make it more difficult for use by men because they typically have larger fingers and hands. Moreover, the amount of pressure exerted to operate cosmetic tweezers is also designed for use by women.

Additionally, most commercially available tweezers are designed for grooming rather than the removal of splinters or other debris that may lodge in the skin. Men are more likely to use tweezers to remove debris that is lodged in the skin as the result of manual labor.

Accordingly, it can be seen that needs exist for improved tweezers that are more suitable for use by men. It is to the provision of solutions to these and other problems that the present invention is primarily directed.

SUMMARY OF THE INVENTION

The present invention is directed to a multi-tool with more than one pair of cooperating tips designed to dig, pull, squeeze, etc., and/or with assemblies to magnify and/or illuminate. In one embodiment of the present invention the multi-tool may include two plates joined by a spring component. In this embodiment, the spring force between the two plates may be about 1.0 to about 2.5 lbs. In a related embodiment, the dig functionality may be performed by a tweezer tip with a sharp end. In still another embodiment of the present invention, the pull functionality may be performed by flat perpendicular pulling tweezer tips. In another embodiment, the squeeze functionality may be performed by rounded-end tweezer tips. In a related embodiment, the illuminate function may be performed by a light assembly and the magnification function may be performed by a magnifying lens assembly. Additionally, the light source used in the illumination function may be adapted to swivel/pivot. In an embodiment of the present invention, the two plates may have a surface coating for better grip.

Figure 1:
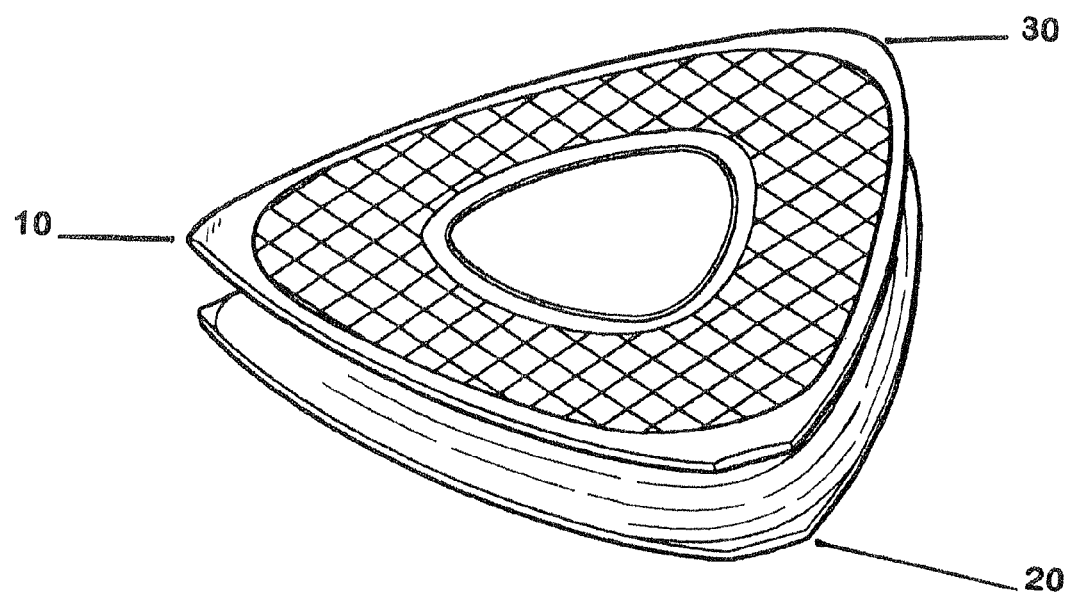
FIG. 1 is a top view of a multi-tool according to a first example embodiment of the present invention.
Figure 2:
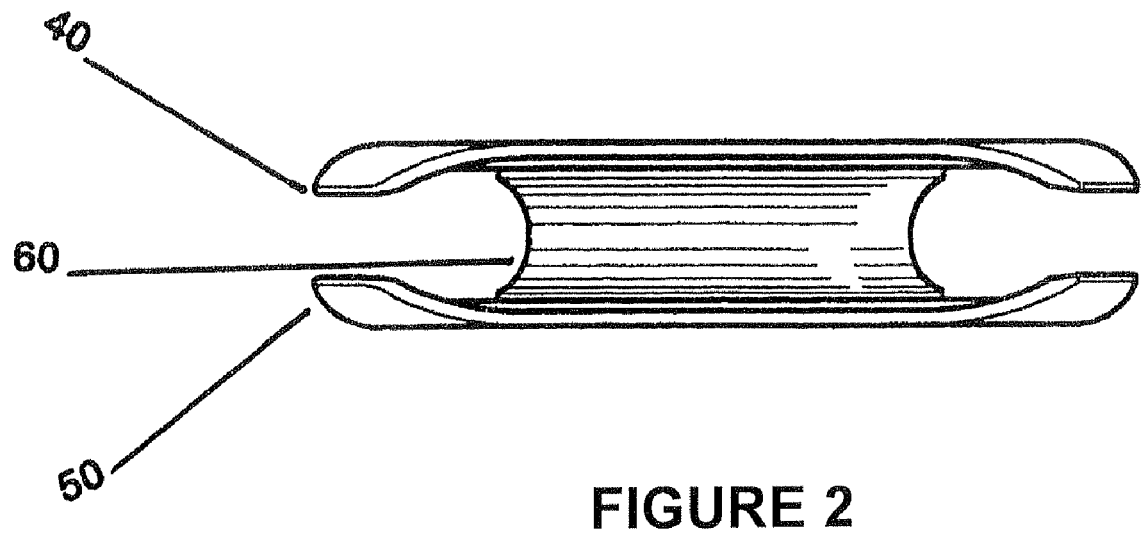
FIG. 2 is a side view of the multi-tool shown in FIG. 1.
Figure 3:
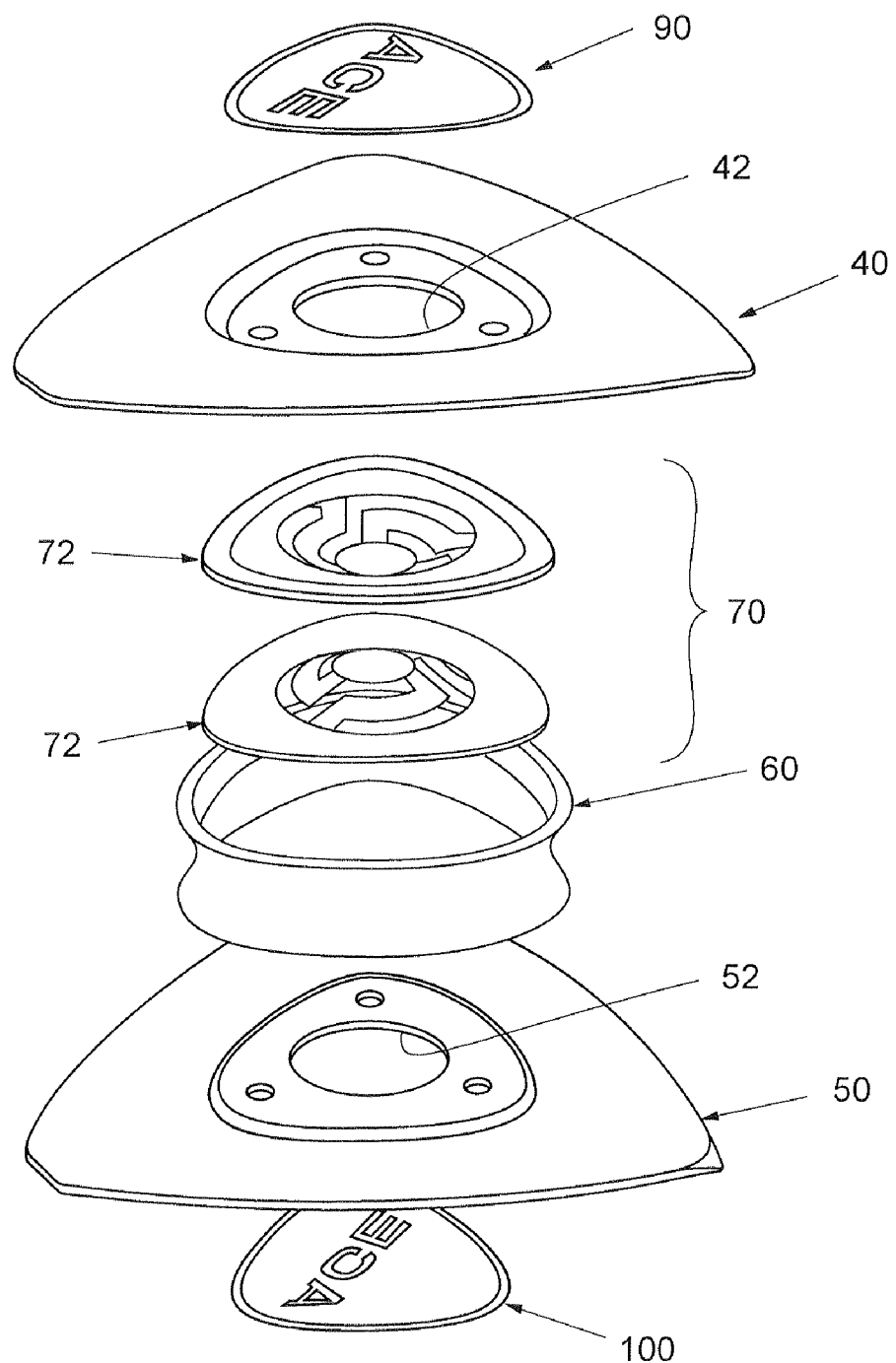
FIG. 3 is an exploded view of the multi-tool shown in FIG. 1.

While the method and device described herein are susceptible to various modifications and alternative constructions, certain illustrative embodiments thereof have been shown in the drawings and will be described below in detail. It should be understood, however, that there is no intention to limit the invention to the specific forms disclosed, but on the contrary, the intention is to cover all modifications, alternative constructions, and equivalents falling within the spirit and scope of the disclosure.

DETAILED DESCRIPTION OF THE DISCLOSURE

The present invention solves the problems listed above by combining multiple specific functions into one tweezer-like apparatus. Any number of functions may be combined and different functions may be used in various embodiments and variations In a specific embodiment of the present invention, three functions may be combined and may be defined by their respective uses. The functions may include magnification, illumination, pulling, digging, and/or squeezing. Pulling, digging, and squeezing may be performed my tweezers of different size and/or angle. In some embodiments, one of these functions may be duplicately-provisioned using different-sized tweezer tips. The multi-tool preferably has two plates each having multiple sides and each in the shape of a triangle, square, pentagon, hexagon or any other multi-sided geometric. Each of the plates has a plurality of tips (outer portions) and corresponding pairs of the tips cooperate to provide the various functions. The present invention combines multiple functions into a handy multi-tool that is preferably pocket-sized.

In one embodiment, a desired function or use may be to remove splinters by a digging motion. Referring to FIG. 1, tip 10 represents a tip that may be used to remove splinters. In this embodiment, the tweezer tip 10 is sufficiently sharp to allow the user to dig into the skin to remove wood, metal, glass, or other debris imbedded into the skin. This same tip 10 may also be used to pluck fine hairs.

In another embodiment of the present invention, one function or use may be to pull, for example, to remove debris or hair from the skin. This tip is preferably designed as a flat perpendicular pulling tweezer, as depicted in FIG. 1 as tip 20. Tip 20 allows the user to remove splinters or other debris from the skin or pluck hair in areas such as the eyebrow, nose, and ear.

In another embodiment, a function, shown as tip 30, may be to squeeze. Tip 30 may be identified by a rounded shape that is useful in squeezing or pinching the skin. Tip 30 may allow the user to squeeze skin afflictions such as embedded debris or minor blisters to remove the fluid trapped between the skin layers. Tip 30 may also allow one to pinch minor skin blood clots for the removal of trapped blood or puss due to injury or to remove blemishes.

Figure 11A:
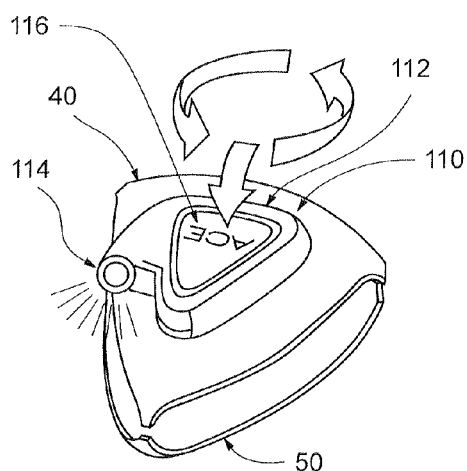
FIG. 11A is a perspective view of a multi-tool according to a fifth example embodiment having a light assembly and a magnifying lens assembly.
Figure 11B:
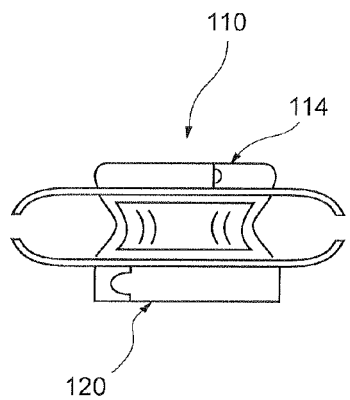
FIG. 11B is a side view of the multi-tool of FIG. 11A.
Figure 11C:
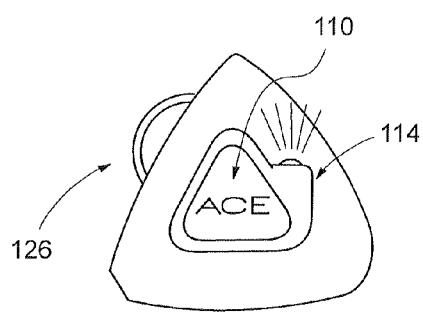
FIG. 11C is a top view of the multi-tool of FIG. 11A showing the light assembly.
Figure 11D:
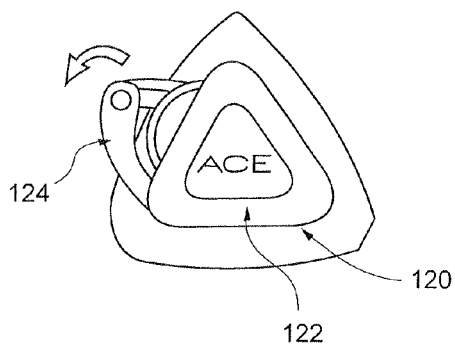
FIG. 11D is a bottom view of the multi-tool of FIG. 11A showing the magnifying lens being removed from a stored position.
Figure 11E:
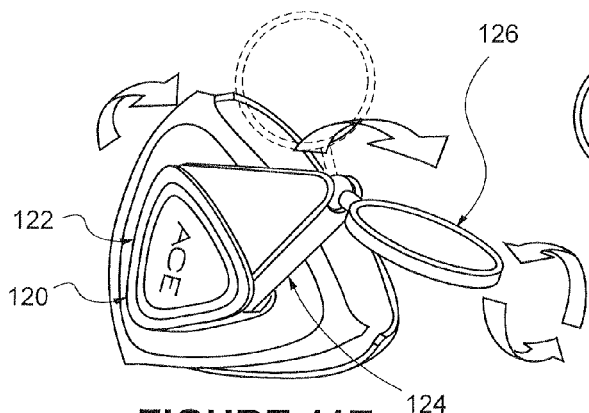
FIG. 11E is a perspective view of the multi-tool of FIG. 11A showing the magnifying lens swiveled from the stored position to an extended position and further swiveled into an aimed position directed at one of the tips.
Figure 11F:
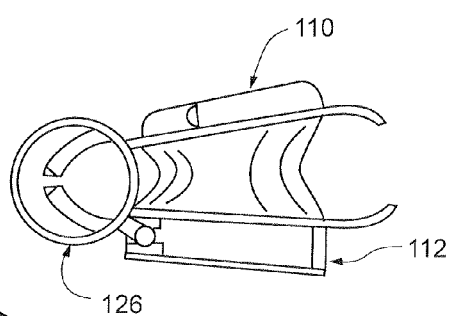
FIG. 11F is a side view of the multi-tool of FIG. 11A showing the magnifying lens in the aimed position of FIG. 11E.

In another embodiment, the multi-tool may possess two different sizes of a specific tweezers tip, such as a very narrow slanted tweezers tip that measures about 0.0625" in width while another side can have a slanted tweezers tip that may measure about 0.200" in width. Additionally, other embodiments may encompass a light feature to illuminate areas of interest such as shadow areas around the eyes or ears, etc. (see for example FIGS. 11A-11C). In some embodiments, the light is adapted to pivot or spin for better illumination. In still another embodiment, a magnifying lens may be incorporated to selectively swivel/pivot and spin into positions over the other tips to allow one to magnify the area of interest (see for example FIGS. 11D-11F).

The multi-tool may have varying surface treatments to provide improved grip for tweezing functions. Exemplary surface treatments may include finger concavities for finger placement, stamped surface textures to improve grip, or soft surface textures to enhance the controlled grip. For example, surface treatments such as santoprene or TPE resins may be over-molded onto the tweezer plates or formed into sheets and attached by adhesives or mechanical attachments such as molded plugs that snap into holes in the tweezer plates.

As shown in FIGS. 3-7B, the present invention includes a spring assembly for the flexible movement which allows the pivoting articulation required to move the tip pairs into close proximity for applying pinching force upon an area of interest. The spring assembly may include a spring component 70 and a gasket 60 (e.g., an annular shroud of TPE or another soft material) "sandwiched" between the tweezers plates 40 and 50 and enclosing the spring component. Gasket 60 is designed to protect the spring component 70 from debris. The spring component 70 is preferably centrally positioned on each of the plates 40 and 50 to provide full 360-degree pivoting motion.

The multi-tweezer tool is preferably comprised of two tweezer plates 40 and 50 that are mirror images of each other with the specific tips of one of the plates aligned with the corresponding tips of the other tweezer plate when assembled. In the depicted embodiment, the plates 40 and 50 are generally triangular and provide three tip pairs 10, 20, and 30. In other embodiments the plates have other shapes and provide other numbers of tip pairs. For example, the plates can be square to provide four tip pairs, the plates can be pentagonal to provide five tip pairs, or the plates can be rectangular or elliptical to provide two tip pairs. And in other embodiments the plates are generally triangular and the spring component is positioned generally at one of the corners to provide two tip pairs at the other two corners. In typical commercial embodiments the plates are stamped and formed of a metal such as stainless steel. In other embodiments the plates are made of hard plastic or another material selected for providing the pinching function. In a typical commercial embodiment, the plates 40 and 50 each have an opening 42 and 52, respectively, that is covered by a cap 90 and 100, respectively, as described in more detail below.

The flexible spring component 70 may be comprised of two spring elements 72 each formed from a sheet of material stock measuring approximately 0.020" to 0.050" in thickness. The thickness of the material stock may be selected depending on the length of the tweezer plate "legs" (from the spring component to the tip) and the thickness of the tweezer plates, so the material stock thickness may be revised per the particular design. In a preferred embodiment, the spring component is designed to require a depression force of between about 1.0 to about 2.5 lbs. as measured from the point where the fingers are positioned to depress the tweezers and as measured from the tips inward with this distance being from about 0.500" to about 0.750" for optimal comfort and function. In this embodiment, the force was measured utilizing a 0.3 mm thick stamped and formed metal stock spring and the distance of depression (the collective distance the two tips travel toward each other) at the tweezers tips ranged from about 0.250" to about 0.375".

Each of the spring elements 72 may be stamped from a single piece of spring steel that is engineered with three specific characteristics. The first characteristic of the spring element 72 is a base 74 that can be attached (e.g., spot-welded) to one of the tweezer plates 40 and 50. The base 74 of the depicted embodiment is a flat peripheral band, though it could alternatively be provided by mounting tabs or other attachment structures.

The second characteristic of the spring element 72 is at least one flexible arm 76. In the depicted embodiment, there are three flexible arms 76, though more or fewer may be provided. Each flexible arm 76 of the depicted embodiment has an outer arm segment 78, an inner arm segment 80, and a middle arm segment 82. The outer arm 78 and the inner arm 80 extend from the base 74 and the central plate 84 (described below), respectively, and are laterally offset from each other so that they are not in alignment. And the middle arm 82 extends laterally between the outer arm 78 and the inner arm 80. With the outer and inner arms 78 and 80 laterally offset from each other and the middle arm 82 extending laterally between them, the middle arm is elongated sufficiently to provide the needed spring action.

The third characteristic is the central plate 84 that is used to bind (e.g., by spot-welding) the two spring elements 72 together in the assembly process. The central plates 84 of the depicted embodiment each have a flat surface for attachment to each other, though alternatively the central plates can be provided with mechanical interlocking elements or other attachment structures. The central plate 84 is preferably positioned generally centrally relative to the base 74, though it need not be precisely centrally located as long as it is within the periphery/footprint of the base.

Figure 4B:
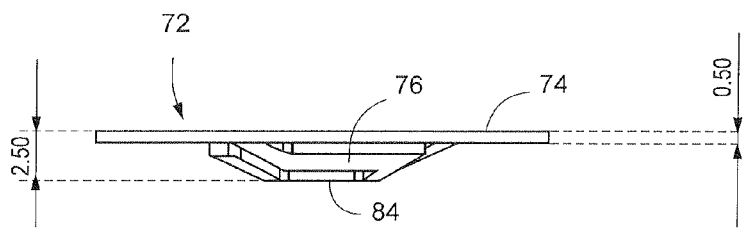
FIG. 4B is a side view of the spring element of FIG. 4A.

In a typical commercial embodiment, the spring element 72 is generally frusto-conical (see FIG. 4B). The base 74 has the shape of an annulus with a generally triangular outer edge and a circular inner edge, the central plate 84 has the shape of a circle, the outer and/or inner arms 78 and 80 are generally radially arranged (generally perpendicular to a tangent to the inner edge of the base 74 and to the central plate 84, respectively), and the middle arm 82 has a curvature that fits the annular gap between the inner edge of the base 74 and the central plate 84 (see FIG. 4C). In this way, the two spring elements 72 are each generally frusto-conical and, when mounted together to form one of the spring components 70, have the general profile of an hour-glass, with the bases 74 being wider than the central plates 84 (see in FIG. 4D). So the plates 40 and 50 can pivot about the spring component 70 in any direction to provide full 360-degree deflection capability. Thus, the user can apply pinching compression forces on the plates 40 and 50 at different locations to selectively bring each of the tip pairs 10, 20, and 30 into close proximity and achieve the precise tweezing action desired.

In alternative embodiments, the spring element is generally frusto-pyramidal, with three, four, or more sides. For example, in an embodiment with triangular plates having three tips, the base and the central plate can be triangular and oriented to provide the desired spring action for the three tips. In another embodiment, the spring element is generally frusto-pyramidal with an octagonal or other polygonal shape.

In other embodiments, the flexible arms have a zig-zag or sinusoidal shape to provide sufficient elongation for the needed spring action. In still other embodiments, the flexible arms have a spiral configuration around a circular central plate to provide sufficient elongation for the needed spring action. And in yet other embodiments, the flexible arms are radially arranged (so that the inner and outer arm segments are generally in-line with each other) and have a lateral extension to provide sufficient elongation for the needed spring action. It will be understood that these and other spring component configurations are contemplated by and within the scope of the present invention.

Figure 5B:
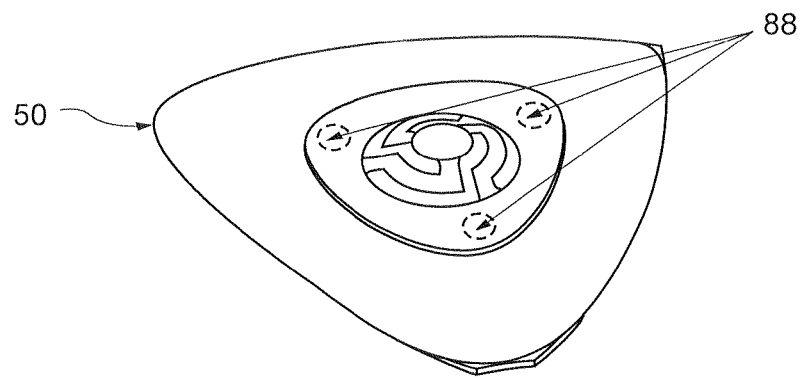
FIG. 5B is a perspective view of a portion of the multi-tool of FIG. 1 showing the assembly step of mounting one of the spring elements to one of the plates.
Figure 5C:
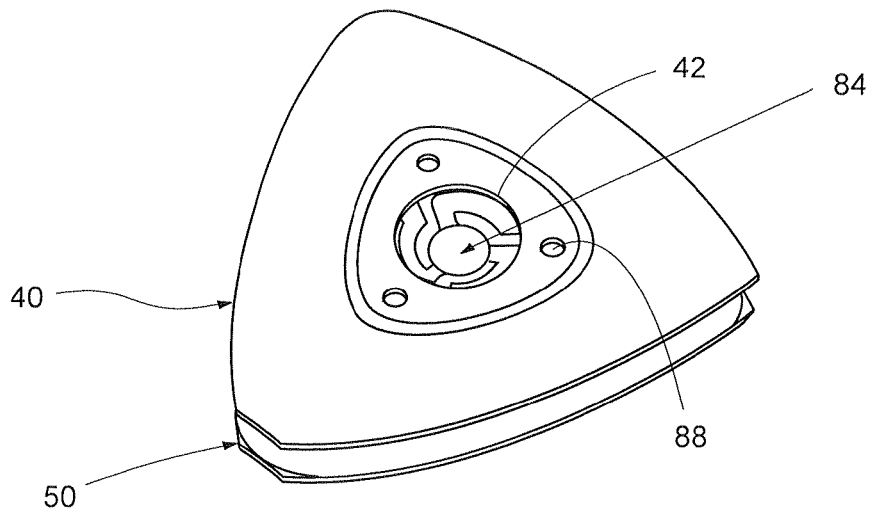
FIG. 5C is a perspective view of a portion of the multi-tool of FIG. 1 showing the assembly step of mounting two of the spring elements together.
Figure 5A:
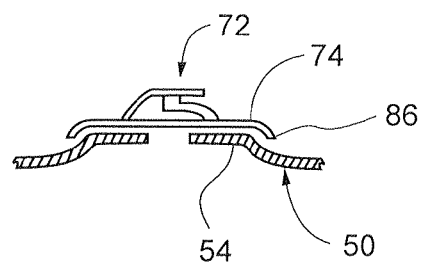
FIG. 5A is a side view of a detail portion of the multi-tool of FIG. 1 showing the mounting arrangement of one of the spring elements to one of the plates.

To assemble the multi-tool tweezer, each of the spring elements 72 may be positioned in the middle of its corresponding tweezer plate 40 or 50 utilizing a specifically designed alignment fixture that properly positions the spring elements and holds them in place while forming them into a subassembly. For example, as shown in FIG. 5A, the plate 50 may include a raised section 54 (e.g., formed by a depression in the opposite side of the plate as depicted or by added thickness) for mounting to the base 84 of the spring element 72. The raised section 54 and the base 84 preferably have conforming shapes so that they seat together in a discrete position, which allows for proper positioning and orientation of the spring element 72 on the plate 50. For example, the base 84 may have an outwardly extending portion (e.g., a peripheral lip or outwardly turned tabs) 86 that mates with the raised section 54 so that the spring element 72 seats in a discrete position on the plate 50.

Once the spring element 72 is positioned on the plate 50, it is then secured in place. For example, the plates 40 and 50 may have more or more through-holes 88 that permit the bases 84 to be spot-welded to the plates 40 and 50, as shown in FIG. 5B.

After spring elements 72 are mounted to both plates 40 and 50, the gasket 60 is positioned around the spring element of one of the tweezer subassemblies and placed in another specifically designed holding fixture, and then the other tweezer subassembly is positioned and precisely aligned (so that the corresponding tips are in alignment with each other) with the first tweezer subassembly within the holding fixture. Then the bases 84 of the spring elements 72 of the two tweezer subassemblies are attached (e.g., by spot-welding) together, as shown in FIG. 5C, with the two tweezer subassemblies trapping the gasket 60 between them. The spot-weld is made possible by through-holes 42 and 52 (e.g., formed by stamping) on the tweezer plates 40 and 50, respectively, thereby allowing access to the central plates 84 of the spring elements 72. The spot-welding operation securely binds the two tweezer subassemblies together. The final assembly step may be the application (e.g., snap-fit, welding, or adhesive) of caps 90 and 100 (e.g., logo plates) over the through-holes 42 and 52 in the plates 40 and 50, as these through-holes are no longer needed. Although in the embodiment described herein the plates and spring elements are made or metal and welded together, it will be understood that the plates can be made of a hard plastic and the spring elements can be made of a flexible plastic, with these parts attached together by an adhesive or another conventional fastening technique.

Figure 6:
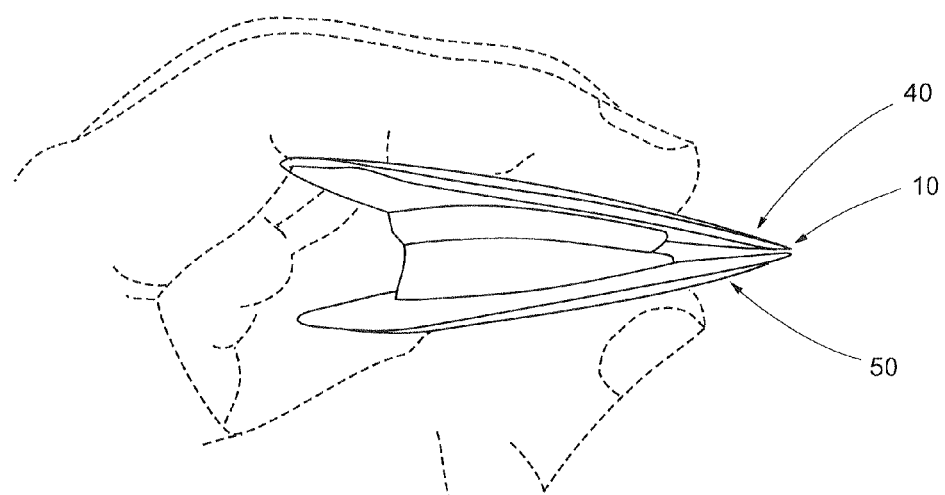
FIG. 6 is a side view of the multi-tool of FIG. 1 showing the multi-tool in use in a deflected position.
Figure 7A:
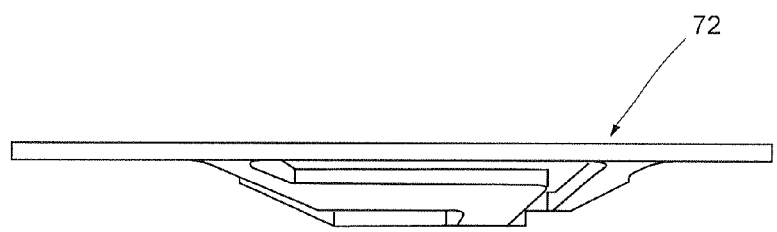
FIG. 7A is a side view of one of the spring elements of the multi-tool of FIG. 1 showing the spring element in a neutral/rest position.
Figure 7B:
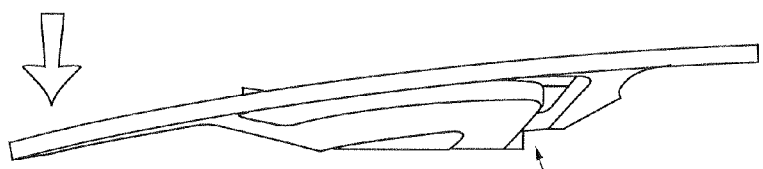
FIG. 7B is a side view of one of the spring elements of FIG. 7A showing the spring element in the deflected position.

FIG. 6 is a side view showing the use of the multi-tool. When a user applies inwardly directed compression forces at first locations (between the spring component and the first tips) on the plates 40 and 50, the spring elements 72 deflect from a neutral/rest position (see FIG. 7A) to a deflected position (see FIG. 7B), permitting the plates to pivot until the first tips 10 come into close proximity with each other in a pinching action. The user can additionally or alternatively apply compression forces at second and third locations (between the spring component and the second tips and between the spring component and the third tips, respectively) on the plates 40 and 50 to cause the second and third tips to come into close proximity with each other in a pinching action.

Figure 8:
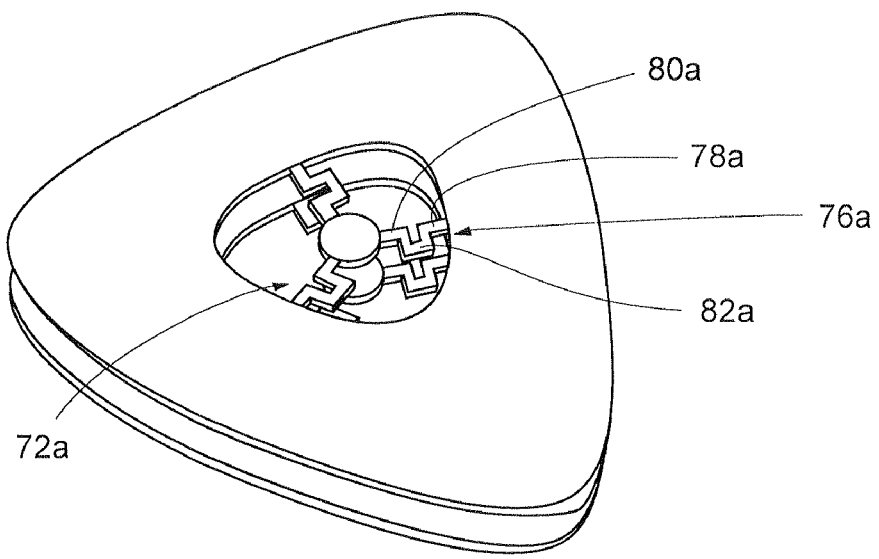
FIG. 8 is a perspective view of a multi-tool according to a second example embodiment, showing an alternative spring element design.

Having described a first example embodiment of the invention, other example embodiments will now be described in some detail. FIG. 8 shows a multi-tool according to a second example embodiment. This embodiment has an alternative spring component design including two spring elements 72*a* that are similar to those of the first embodiment. But in this embodiment the flexible arms 76*a* have a different shape. In particular, the outer and inner arm segments 78*a* and 80*a* are generally radially arranged (so that they are generally in-line with each other) and the middle arm segment 82*a* has a lateral loop extension to provide sufficient elongation for the needed spring action.

Figure 9:
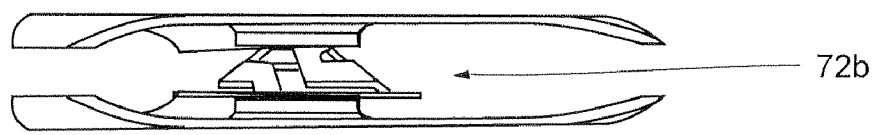
FIG. 9 is a side view of a multi-tool according to a third example embodiment having a single spring element.

FIG. 9 shows a multi-tool according to a third example embodiment. This embodiment has a spring component that is similar to that of the first embodiment. But in this embodiment the spring component consists of only a single of the spring elements 72*b* and it is larger (with a larger base-to-central plate dimension) than those of the first embodiment.

Figure 10:
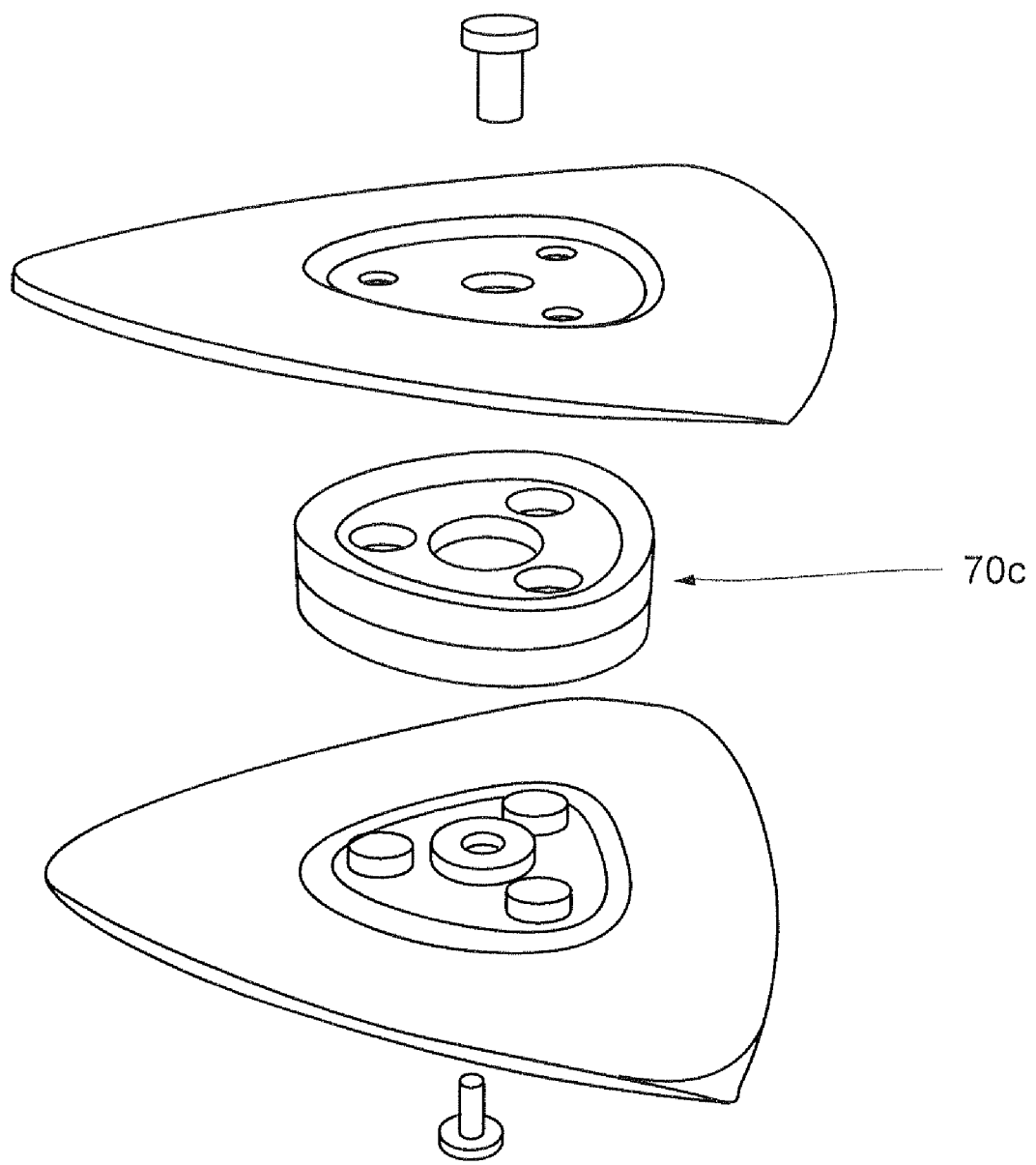
FIG. 10 is an exploded view of a multi-tool according to a fourth example embodiment having an elastomeric spring element.

FIG. 10 shows a multi-tool according to a fourth example embodiment. In this embodiment the spring component is substantially different from those described above. In particular, the spring component 70c of this embodiment is provided by an elastomeric spring element. For example, the spring component 70c may be provided by a triangular or circular disk-shaped piece of an elastomeric material that is mounted to the plates by pins.

FIGS. 11A-11F show a multi-tool according to a fifth example embodiment. This embodiment may include any type of spring component including any of those described herein. In addition, this embodiment includes a light assembly 110 and a magnifying lens assembly 120. It will be understood that multi-tools can be provided with the light assembly 110 but not the magnifying lens assembly 120, with the magnifying lens assembly but not the light assembly, with multiple ones of the light assembly and/or the magnifying lens assembly, or with another design of a light assembly and/or a magnifying lens assembly.

The light assembly 110 of the depicted embodiment includes a housing 112 with a light source 114 and a control 116. The light source 114 may be provided by an LED or other light-emitting device that is powered by at least one disposable or rechargeable battery (not shown) in the housing 112. The control 116 may be provided by an on-off pushbutton switch or another conventional activation control switch that is electrically connected between the light source 114 and the battery. The housing 112 is made of metal, plastic, or another suitable material. The housing 112 is mounted to one of the plates 40 or 50 by a swivel coupling that permits the housing to be swiveled (as indicated by the directional arrows of FIG. 11A) in a plane parallel to the plates to direct the light source 114 at an area of interest while at the same time manipulating the plates to tweeze the illuminated area (see FIG. 11F).

The magnifying lens assembly 120 of the depicted embodiment includes a housing 122 that is fixedly mounted to one of the plates and that houses an extension 124 and a magnifying lens 126. The housing 122 is made of metal, plastic, or another suitable material. The magnifying lens 126 may be of a conventional type made of glass, plastic, acrylic, or another suitable material to provide a magnification of 2×, 3×, 10×, or another magnification power as may be desired. The extension 124 is preferably sized and shaped to receive the magnifying lens 126 therein and fit within the housing 122. The extension 124 is mounted to the housing 112 by a swivel coupling that permits the extension to be swiveled (as indicated by the directional arrow of FIG. 11D) in a plane parallel to the plates from a stored position to an extended position. And the magnifying lens 126 is mounted to the extension 124 by a swivel coupling that permits the magnifying lens to be swiveled (as indicated by the center directional arrow and phantom-shown magnifying lens of FIG. 11E) in a plane parallel to the plates from a stored position within the extension to an extended position and that permits the magnifying lens to be swiveled (as indicated by the right directional arrows of FIG. 11E) through a 360-degree range of motion. In this way, the magnifying lens 126 can be swiveled into an aimed position directed at an area of interest while at the same time manipulating the plates to tweeze the magnified area (see FIGS. 11E and 11F).

In an alternative embodiment, the magnifying lens housing is mounted to one of the plates by a swivel coupling and the magnifying lens is mounted directly to the housing (without an extension) by a swivel coupling. In another alternative embodiment, the magnifying lens assembly includes two or more magnifying lenses of different powers and the housing is sized and shaped to receive all of the magnifying lenses.

Figure 12A:
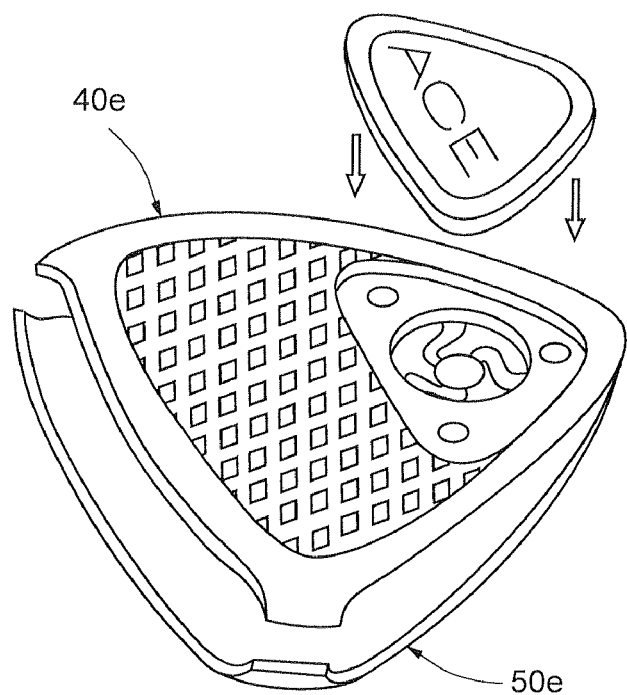
FIG. 12A is a perspective view of a multi-tool according to a sixth example embodiment having a two tip pairs and an off-center spring component.
Figure 12B:
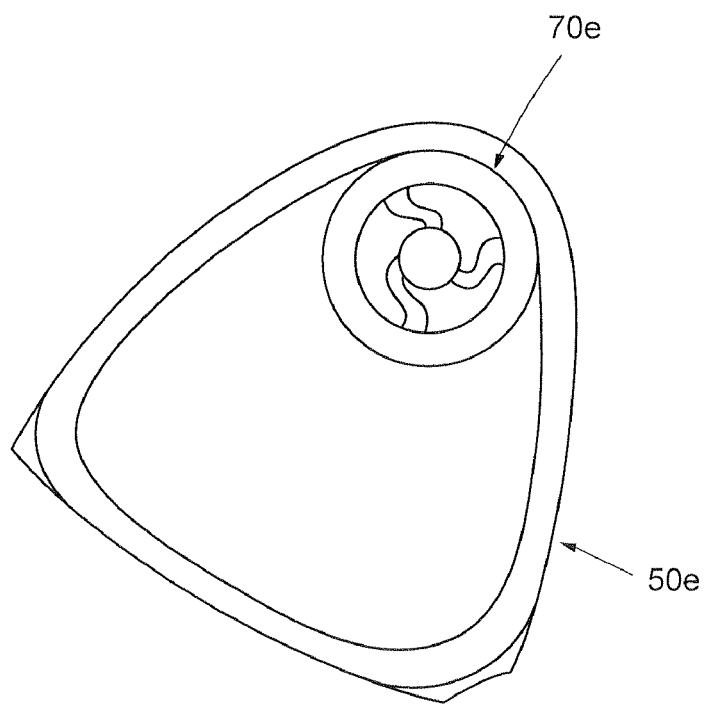
FIG. 12B is a top view of one plate and spring element subassembly of the multi-tool of FIG. 12A.
Figure 13A:
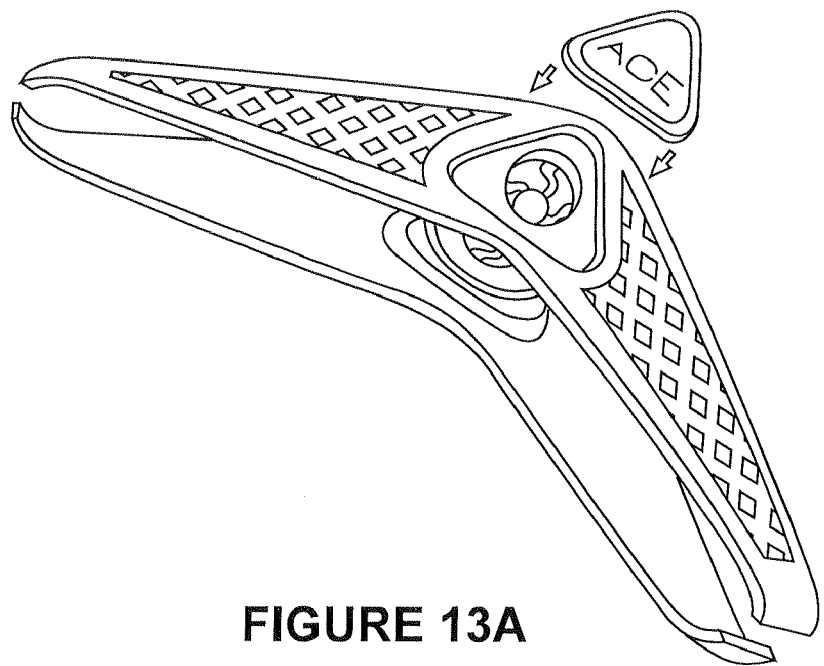
FIG. 13A is a perspective view of a multi-tool according to a seventh example embodiment having a two tip pairs and an off-center spring component.
Figure 13B:
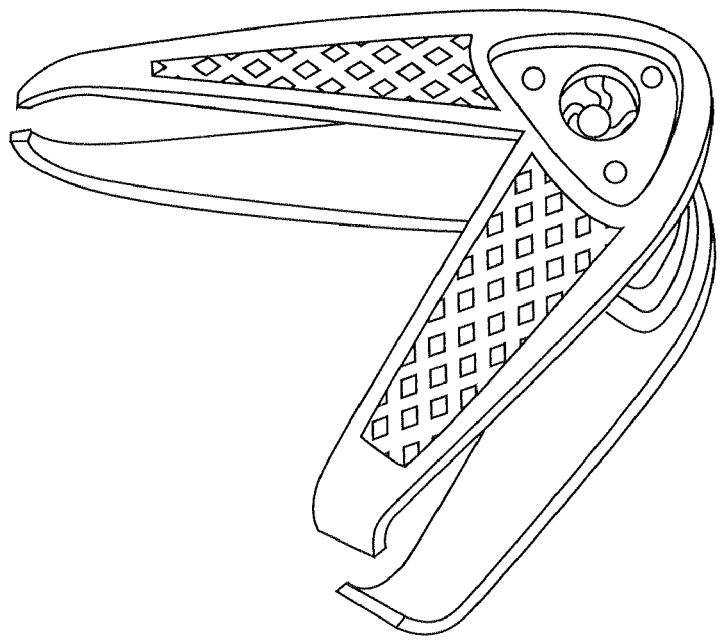
FIG. 13B is a perspective view of an alternative to the multi-tool of the seventh example embodiment of FIG. 13A.

FIGS. 12A and 12B show a multi-tool according to a sixth example embodiment. This embodiment is similar to those of the above-described embodiments. But in this embodiment the plates are generally triangular with two tip pairs in two of the corners and with the spring component positioned in the other corner. The plates can alternatively be V-shaped (see for example FIGS. 13A and 13B) or triangularly oblong (e.g., a 30/75/75 triangle).

Figure 4C:
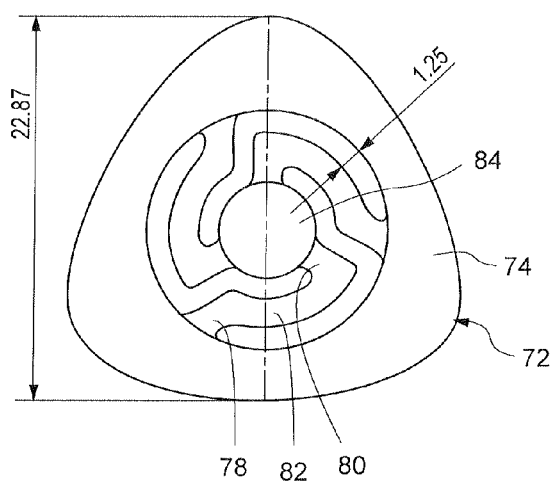
FIG. 4C is a plan view of the spring element of FIG. 4A.
Figure 4A:
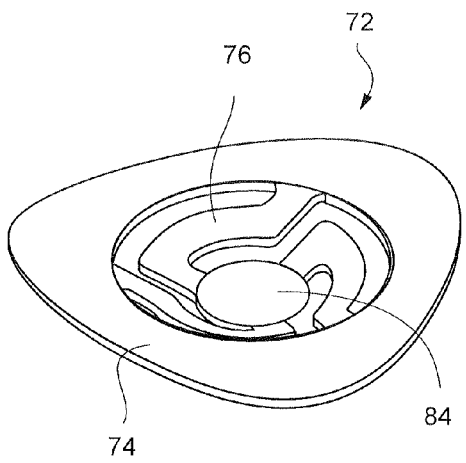
FIG. 4A is a perspective view of a spring element of the multi-tool shown in FIG. 1.
Figure 4D:
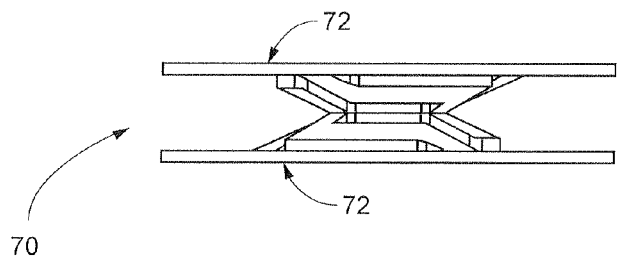
FIG. 4D is a side view of a spring component formed by two of the spring elements of FIG. 4A.

As used herein, the term "tips" means outer portions of the plates. As such, the tips may be located at corners or at sides (between the corners) of the plates. In addition, the terms "tip" and "tip pairs" are used interchangeably herein. In some embodiments, one or more of the functionalities provided by the tips may be accomplished by providing only one tip. For example, the digging function may be accomplished with only one sharp tip, and in some embodiments only one of the plates has the sharp "digging" tip. Furthermore, the dimensions (in mm) shown in FIGS. 4B-4C are those of a typical commercial embodiment and are representative of the invention but are not intended to be limiting of the invention as the spring elements may be provided in other dimensions.

It is to be understood that this invention is not limited to the specific systems, methods, conditions, or parameters described and/or shown herein, and that the terminology used herein is for the purpose of describing particular embodiments by way of example only. Thus, the terminology is intended to be broadly construed and is not intended to be unnecessarily limiting of the claimed invention. For example, as used in the specification including the appended claims, the singular forms "a," "an," and "one" include the plural, the term "or" means "and/or," and reference to a particular numerical value includes at least that particular value, unless the context clearly dictates otherwise. In addition, any methods described herein are not intended to be limited to the sequence of steps described but can be carried out in other sequences, unless expressly stated otherwise herein.

While the present invention has been described with reference to specific examples, which are intended to be illustrative only and not to be limiting of the invention, it will be apparent to those of ordinary skill in the art that changes, additions or deletions may be made to the disclosed embodiments without departing from the spirit and scope of the invention.

The invention claimed is:

1. A multi-tool tweezer, comprising:
   a first plate with a first tip and a second tip;
   a second plate with a first tip and a second tip; and
   a spring component mounted between the first plate and the second plate to permit the first tips to be forced into close proximity in a first pinching action and to permit the second tips to be forced into close proximity in a second pinching action wherein the spring component has a generally frusto-conical shape in a direction between the first and second plates,
   wherein the spring component comprises a base, a central plate, and at least one flexible arm extending between the base and the central plate, the spring component having the generally frusto-conical shape between the base and the central plate
   wherein the flexible arm includes an outer arm segment extending inwardly from the base, an inner arm segment extending outwardly from the central plate and circumferentially and radially offset from the outer arm segment, and a middle arm segment extending radially between the outer and inner arm segments.

2. The multi-tool of claim 1, wherein the spring component comprises first and second of the spring components, wherein the first and second bases are mounted to the first and second plates and the first and second central plates are mounted to each other.

3. A multi-tool tweezer comprising:
- a first generally triangular plate with a first tip, a second tip, and a third tip;
- a second generally triangular plate with a first tip, a second tip, and a third tip, wherein the first and second plates are arranged with their respective first, second, and third tips in opposing alignment; and
- a spring component mounted between the first plate and the second plate, wherein the spring component comprises first and second spring elements each including a base, a central plate, and at least one flexible arm extending between the base and the central plate, wherein the first and second bases are mounted to the first and second plates and the first and second central plates are mounted to each other, and
- wherein the first plate and the second plate can pivot about the spring component in any direction providing full 360-degree deflection allowing a user to apply pinching compression forces on the plates at different locations to permit the first, second, and third pairs of tips to be selectively forced into close proximity in respective first, second, and third pinching actions.

4. The multi-tool of claim 3, wherein each of the flexible arms include an outer arm segment extending inwardly from the corresponding base, an inner arm segment extending outwardly from the corresponding central plate and circumferentially and radially offset from the outer arm segment, and a middle arm segment, extending laterally between the outer and inner arm segments.

5. The multi-tool of claim 4, wherein the base and the central plate of each spring element define an annular gap therebetween and the middle arm segment of each spring element is disposed within the respective annular gap.

6. The multi-tool of claim 4, wherein the inner arm segment and the outer arm segment of each spring element are generally radially arranged and each spring element is generally frusto-conical between the respective base and central plate.

7. The multi-tool of claim 3, wherein each of the bases is provided by a flat peripheral band with a generally circular inner edge.

8. The multi-tool of claim 3, wherein each of the central plates is generally circular and has a flat mounting surface.

9. The multi-tool of claim 3, wherein each of the spring elements has a generally frusto-conical shape.

10. The multi-tool of claim 3, wherein the spring component is mounted to each of the plates generally centrally between the respective first, second, and third tips.

11. The multi-tool of claim 3, wherein the first, second, and third tips respectively comprise sharp tips for digging, flat perpendicular second tips for pulling, and round third tips for squeezing.

12. The multi-tool of claim 3, further comprising a gasket mounted between the plates and surrounding the spring component.

* * * * *